(12) United States Patent
Ogonowsky

(10) Patent No.: US 7,058,992 B1
(45) Date of Patent: Jun. 13, 2006

(54) SKI GOGGLES WITH OPENING FOR EARS

(76) Inventor: Brian D. Ogonowsky, 307 N. Clark Ave., Los Altos, CA (US) 94022

( * ) Notice: Subject to any disclaimer, the term of this patent is extended or adjusted under 35 U.S.C. 154(b) by 9 days.

(21) Appl. No.: 10/945,228

(22) Filed: Sep. 20, 2004

(51) Int. Cl.
*A61F 9/02* (2006.01)

(52) U.S. Cl. .................. 2/448; 2/209; 351/123
(58) Field of Classification Search ............ 2/209, 2/13, 448, 452; 351/123, 156
See application file for complete search history.

(56) References Cited

U.S. PATENT DOCUMENTS

| | | | | |
|---|---|---|---|---|
| 1,621,629 A | * | 3/1927 | Dawson | 2/448 |
| 3,605,204 A | * | 9/1971 | Amundsen | 24/171 |
| 4,077,068 A | * | 3/1978 | Anderson | 2/428 |
| 4,670,911 A | | 6/1987 | Dunford | |
| 4,682,374 A | * | 7/1987 | Geiser | 351/123 |
| 5,162,823 A | * | 11/1992 | Goldstein | 351/123 |
| 5,302,977 A | * | 4/1994 | Markovitz et al. | 351/114 |
| 5,813,056 A | * | 9/1998 | Ambrose | 2/452 |
| 6,952,841 B1 | * | 10/2005 | Schary et al. | 2/452 |

* cited by examiner

*Primary Examiner*—Katherine M. Moran

(57) ABSTRACT

A strap for ski goggles is disclosed wherein the strap includes a ring at the location of the wearer's ears so that the ring surrounds or substantially surrounds the ear. In this way the strap does not press down on the ears. The ring may include a Velcro perimeter that engages a corresponding Velcro perimeter of a removable ear cup for keeping the ears warm. The rings may be circular, oval, or generally U-shaped.

18 Claims, 1 Drawing Sheet

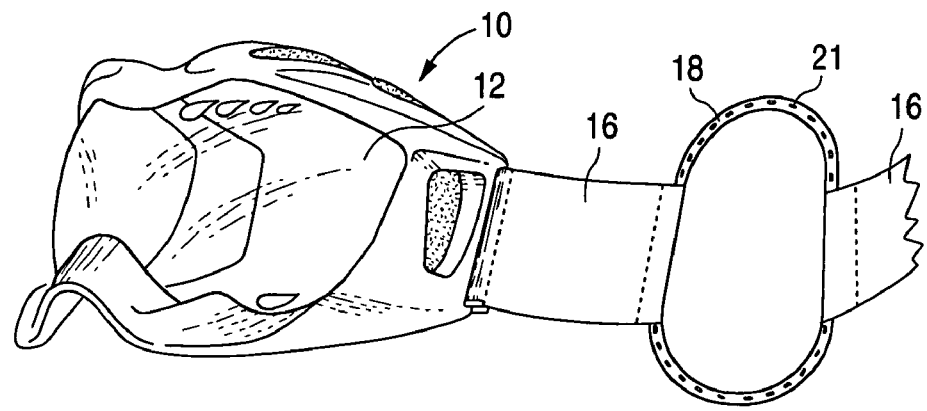
FIG. 1
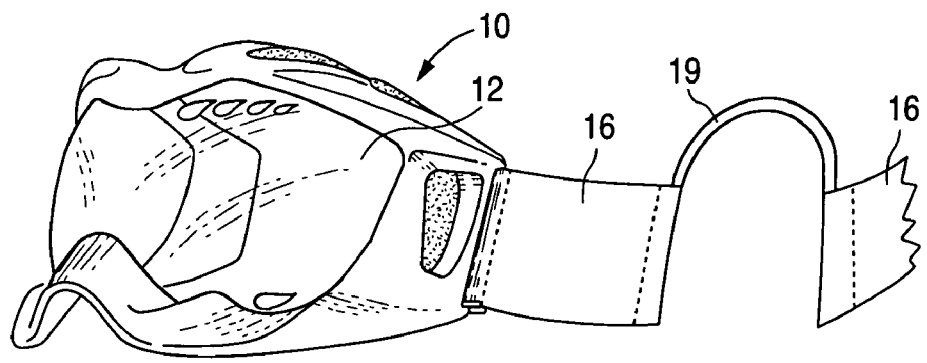
FIG. 2
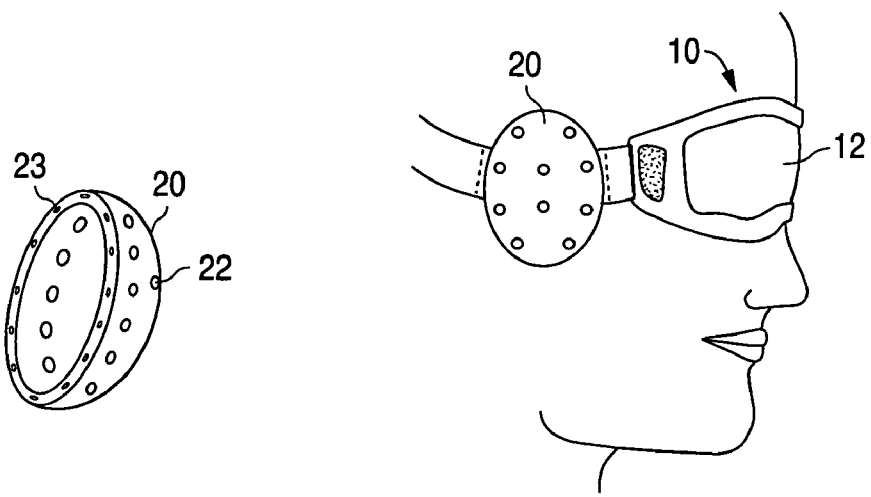
FIG. 3     FIG. 4

SKI GOGGLES WITH OPENING FOR EARS

FIELD OF THE INVENTION

This invention relates to ski goggles and, in particular, to the ski goggle strap.

BACKGROUND

Conventional ski goggles have a wide elastic strap that is placed over the wearer's ears and the back of the wearer's head to keep the ski goggles securely in place. After some time, the pressure exerted by the strap on the ears becomes irritating.

Ski goggles are known that include an ear muff attachment. In such devices (e.g., described in U.S. Pat. No. 4,682,374), the strap presses down on the ear muffs. Further, the ear muffs are only worn when it is very cold and they limit the ears' sound sensitivity.

SUMMARY

A strap for ski goggles is disclosed wherein the strap includes a ring at the location of the wearer's ears so that the ring encircles or substantially encircles the ear. In this way the strap does extend over the ears and does not press down on the ears. The rings may be circular, oval, or generally U-shaped.

The ring may include a Velcro perimeter that engages a corresponding Velcro perimeter of a removable ear cup for keeping the ears warm.

BRIEF DESCRIPTION OF THE DRAWINGS

FIG. 1 is a perspective view of one example of ski goggles having a strap that includes a ring that encircles each ear.

FIG. 2 is a perspective view of an example of ski goggles having a strap that includes a U-shaped ring that substantially encircles each ear.

FIG. 3 is a perspective view of an ear cup that is removably secured to the ring of FIG. 1.

FIG. 4 is a side view showing a person wearing the ski goggles of FIG. 1 with the ear cup attached.

DETAILED DESCRIPTION

FIG. 1 illustrates any conventional ski goggles 10 having a frame with a lens 12. The present invention may be used with any type of ski goggles.

A conventional elastic strap 16 stretches to provide a snug fit around the wearer's head. The elastic strap 16 is typically a synthetic cloth interwoven with a rubber material.

The elastic strap 16 is connected to a flexible ring 18, one for each ear. The connection mechanism may be the end of the elastic strap 16 looped around ring 18 and sewn in place. Ring 18 may be made of a flexible plastic covered with a spongy material for added comfort. Alternatively, ring 18 may be a bendable wire coated with a soft material so that ring 18 may be custom fitted to the wearer's head. Many other structures can be used for ring 18 so that it generally retains its shape when pulled by elastic strap 16 yet is comfortable to the wearer.

In the illustrated embodiment, each ring 18 is sized to completely encircle the wearer's ear so that no portion of the elastic strap 16 presses down on the ear.

In an alternative embodiment, shown in FIG. 2, the ring portion 19 generally forms a U-shape (including any incomplete circle shape) rather than a circle or oval. In such a case, the ring substantially encircles the ear. The generally U-shaped ring portion 19 may be advantageous for a more universal fit.

FIG. 3 illustrates a plastic or synthetic-cloth ear cup 20 that is removably secured to ring 18 using any suitable method. In one embodiment, the outward facing perimeter of ring 18 is covered with a Velcro strip 21 and secured with an adhesive. The perimeter of the ear cup 20 has a corresponding Velcro strip (e.g., hooks or loops) 23 that engages the Velcro strip 21 on ring 18. The ear cup 20 can be secured over ring 18 to keep the wearer's ears warm. The ear cup 20, in one embodiment, has holes 22 in it to allow air and sounds to penetrate the ear cup. The ear cups 20 may also protect the ears in case of a fall.

FIG. 4 is a side view of a wearer, showing the opposite side of the goggles of FIG. 1 and showing how the ring 18 and cup 20 fit completely over the wearer's ears to avoid any irritation from the elastic strap putting pressure on the ears. No downward pressure on the ear or on the area surrounding the ear is exerted by the strap 16 since strap 16 does not overlie the ring 18 or ear cup 20.

Having described the invention in detail, those skilled in the art will appreciate that, given the present disclosure, modifications may be made to the invention without departing from the spirit and inventive concepts described herein. Therefore, it is not intended that the scope of the invention be limited to the specific embodiments illustrated and described.

What is claimed is:

1. Goggles comprising:
    a frame portion housing a lens;
    a strap attached to the frame; and
    two rings attached to the strap such that the strap does not extend over a wearer's ears, each ring being attached to the strap at a location which coincides with the location of an ear of a wearer, each ring having a size such that the wearer's ear protrudes through the ring without the strap or the ring pressing on the wearer's ear,
    the strap forming a plurality of sections, the rings comprising a first ring and a second ring, a first section of the strap being attached at one end to a first portion of the first ring and to a first portion of the frame, a second section of the strap being attached at one end to a first portion of the second ring and to a second portion of the frame, a third section of the strap being attached at one end to a second portion of the first ring and a second portion of the second ring, the third section of the strap for extending around a back of a wearer's head to secure the frame to the wearer's face.

2. The goggles of claim 1 wherein each ring is flexible.

3. The goggles of claim 1 wherein each ring has an attachment mechanism for attachment to an ear cup.

4. The goggles of claim 1 further comprising an ear cup for attachment to the rings.

5. The goggles of claim 4 wherein the ear cup comprises a plastic cup with holes for surrounding the wearer's ear.

6. The goggles of claim 4 wherein each of the rings has one of a hook or loop portion and each ear cup has one of a hook or loop portion for attachment to the hook or loop portion on the rings.

7. The goggles of claim 1 wherein the rings comprise a wire.

8. The goggles of claim 1 wherein the rings comprise a plastic.

9. The goggles of claim 1 wherein the rings have a generally circular or oval shape.

10. The goggles of claim 1 wherein the rings have a generally U-shape.

11. A method for supporting goggles on a wearer's face including the steps of: comprising:
providing goggles having a strap attached to a frame and having two rings attached to the strap, each ring being attached to the strap at a location which coincides with the location of an ear of a wearer, each ring having a size such that the wearer's ear protrudes through the ring without the strap or the ring pressing on the wearer's ear, a portion of the strap for extending around the back of a wearer's head for securing the goggles to the wearer's face; and
placing the frame over the wearer's face with the strap securing the frame to the wearer's face by the strap extending around the back of the wearer's head such that the wearer's ears protrude through a respective ring so that the strap and rings do not press on the wearer's ears.

12. The method of claim 11 wherein each ring is flexible.

13. The method of claim 11 further comprising attaching an ear cup to each ring, the car cup surrounding an ear of the wearer.

14. The method of claim 13 wherein the attaching comprises attaching each ring to a respective ear cup with a hook and loop attachment mechanism.

15. The method of claim 11 wherein the rings comprise a wire.

16. The method of claim 11 wherein the rings comprise a plastic.

17. The method of claim 11 wherein the rings have a generally circular or oval shape.

18. The method of claim 11 wherein the rings have a generally U-shape.

* * * * *